United States Patent [19]

Seidel

[11] Patent Number: 4,797,254

[45] Date of Patent: Jan. 10, 1989

[54] PROTECTION MEANS FOR A PROCESS ANALYZER SYSTEM

[75] Inventor: Rudolf Seidel, Basel, Switzerland

[73] Assignee: Benke Instrument & Elektro Ag, Pratteln, Switzerland

[21] Appl. No.: 23,391

[22] Filed: Mar. 9, 1987

[30] Foreign Application Priority Data

Mar. 24, 1986 [DE] Fed. Rep. of Germany ....... 3609929

[51] Int. Cl.$^4$ ............................................. G01N 37/00
[52] U.S. Cl. ..................... 422/49; 422/63; 422/81; 422/104; 422/117; 435/289; 435/291; 435/809
[58] Field of Search ............ 422/49, 50, 81, 63, 422/64, 67, 104, 117; 312/223, 820; 435/809, 289, 291

[56] References Cited

U.S. PATENT DOCUMENTS

| | | | |
|---|---|---|---|
| 2,789,024 | 4/1957 | Heisler | 312/320 |
| 2,987,364 | 6/1961 | Fall | 312/320 |
| 3,193,358 | 7/1965 | Baruch | 422/64 |
| 3,842,679 | 10/1974 | Iwao et al. | 312/223 |
| 4,033,825 | 7/1977 | Haddad et al. | 435/809 |
| 4,118,280 | 10/1978 | Charles et al. | 435/809 |
| 4,483,927 | 11/1984 | Takekawa et al. | 422/64 |
| 4,517,160 | 5/1985 | Galle et al. | 422/104 |
| 4,621,876 | 11/1986 | Reimer | 312/320 |
| 4,720,463 | 1/1988 | Farber et al. | 435/809 |

*Primary Examiner*—Michael S. Marcus
*Attorney, Agent, or Firm*—Bell & Arkin

[57] ABSTRACT

A sheltered-type protection means for process instrumentation/automation, particularly quality measuring equipment for industrial processes with a hazardous environment and materials is described, which has a self-supporting housing with an extractable support member, on which is arranged at least one analyzer, a sample preparation means, an auxiliary material system and a unidirectional or bidirectional communications means for electrical signals. This arrangement permits a very compact construction and ensures that after extracting the support member unimpeded access to the individual components is possible. The invention also has the advantage that as a result of the small dimensions of the housing, it can be constructed in an extremely tight manner, so that the interior thereof is scavenged e.g. with an inert gas and can be kept under overpressure without leakage losses occurring. Thus, as the entire inner area is protected against explosions, there is no need to provide the individual components of the system in explosionproof and therefore expensive construction forms. The invention satisfies the requirement of being able to install the analyzer system in the immediate vicinity of the particular process and this covers both explosion protection and the necessary protection against the weather.

17 Claims, 4 Drawing Sheets

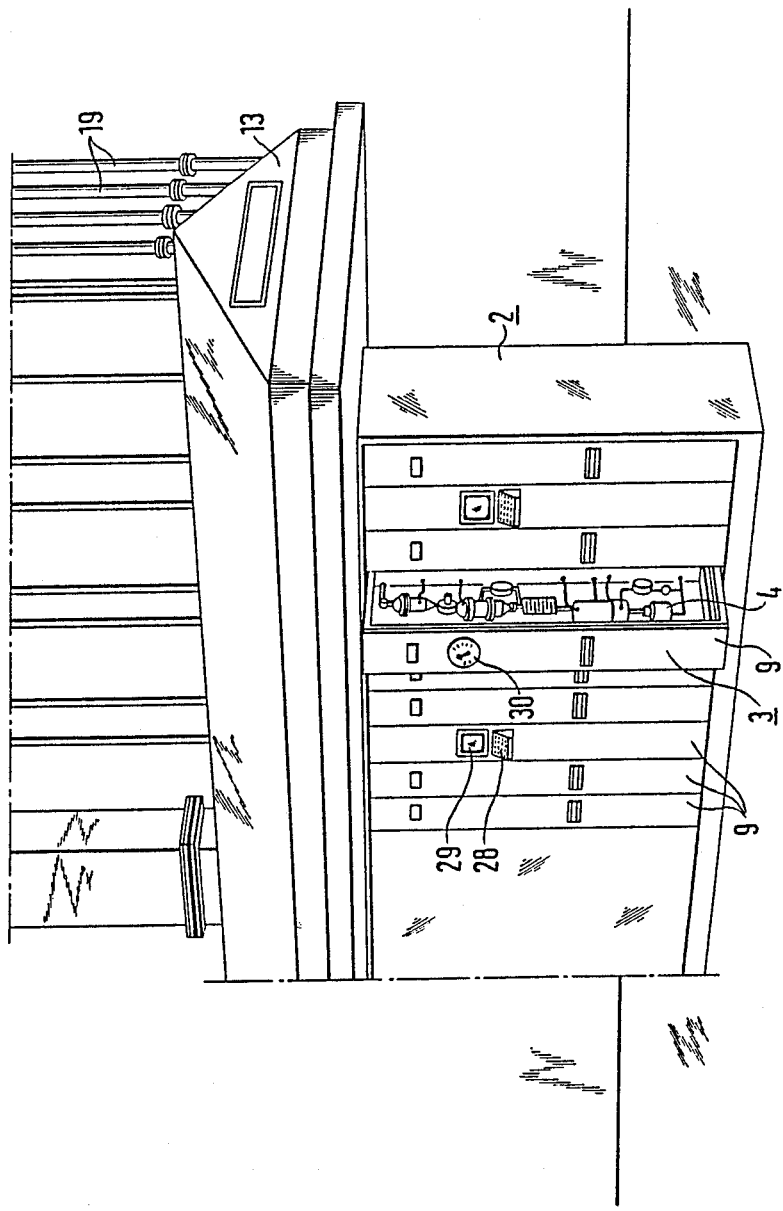

PROTECTION MEANS FOR A PROCESS ANALYZER SYSTEM

FIELD OF THE INVENTION

The present invention relates to an explosionproof process analyzer process analyzer system with process instrumentation/automation units, with at least one process analyzer and with protection means for use in a hazardous environment, e.g. a flammable or explosive environment and/or for use with dangerous materials, e.g. those prejudicial to health.

The protection means protects the environment of the analyzer system and operating personnel against dangerous materials located in the units. The protection means also protects the measuring equipment against dangerous materials in the environment. This is particularly important in the case of so-called open air installations, such as refineries or exploration zones, as well as in buildings in the chemical and pharmaceutical industries.

The process instrumentation and automation units are used for measuring, regulating and controlling process sequences. Process analyzers carry out automatic analyses of materials or material samples and for this purpose it is necessary to make ready and suply process preparation systems, auxiliary material or adjuvant systems and disposal systems. Apart from processes in the hydrocarbon industry, process analyzer systems can also be used in connection with processes related to the processing of explosives and processes using pulverulent, toxic, carcinogenic or otherwise health-prejudicial and hazardous materials. The equipments used are classified by industrial legislation as requiring monitoring.

Possible analysis and measuring processes which may be involved are the known chemical analysis used for establishing chemical affinities or reactions and electrochemical measuring processes, such as e.g. potentiometry, coulometry, voltametry, amperometry or polarography, frequently associated with titrations. Analyses can also relate to the interaction of atoms and molecules with electromagnetic radiation, the excitation of electron transitions and energy states by energy irradiation, as well as emission and absorption. A process analyzer can also investigate the reaction of the material to be investigated on electrical or magnetic fields, the mass spectrum, electrical conductivity, dielectricity and paramagnetism. Finally thermal and mechanical quantities are measured.

BACKGROUND OF THE INVENTION

It is known to install such analyzer systems in central or non-central laboratories. If analysis is performed in a central location within the processing plant, then samples must individually be taken from the process and transported by somebody into the laboratory for feeding into the analyzer system. However, during transportation the state of the sample can change. It is also disadvantageous that there is an unavoidable time delay between taking the sample and analysis. It is also disadvantageous that only individual samples can be analyzed, so that only stochastic measurements are possible. Attempts have therefore been made to install and operate the analyzer system in situ, which offers the possiblity of using process analyzers for continuous analyses and the measuring process can be both continuous and discontinuous with finite measuring cycles. It is known for this purpose to house the system in a fixed, walled or transportable container-comprising structure called "an analyzer shelter". Such a transportable analyzer shelter is described e.g. in a brochure entitled "Analyzer Shelter", issued in November 1981 by Benke Instrument and Elektro AG, of Pratteln, Switzerland. These analyzer shelters can be entered for the purpose of servicing and maintaining analyzers and auxiliary equipment. Although they are ideally suited for many applications, such relatively large-volume arrangements can also have disadvantages.

One of the disadvantages is that complicated and costly precautions have to be taken in view of the hazardous and health-prejudicial materials. The protection costs are much higher than e.g. in the case of instrumentation means, merely processing electrical signals. For the latter it is virtually merely necessary to have an adequate explosion protection and possibly a protection against the penetration of the external atmosphere.

Process analyzers or installation in an area where there is an explosion risk must satisfy the protection types and construction features indicated in the explosion protection regulations, which appear in the following industrial standards: VDE 0 165, 0 171; EN 50014 to 50020, 50028, 50039 and IEC 79-10.

Furthermore, process analyzers must for measuring reasons be protected against environmental influences in order to ensure measuring accuracy, stability and reproductivity of the measurements and to obviate premature aging of the electronic components. For economic and safety reasons apart from protection against the weather, it is also necessary to protect against aggressive or corrosive atmospheres.

In practice, protection is achieved in that separate explosionproof analyzers are placed in analyzer shelters and attempts are made to ventilate the shelters, which attempts have hitherto been very inadequate or involved considerable expenditure. Therefore, analyzer shelters are often only ventilated by natural ventilation. In the case of shelters containing several analyzer systems, a forced ventilation by explosionproof fans is also known. For forced scavenging purposes, for economic reasons air is taken out of the environment and must be cleaned, filtered, dried and treated as a function of its state. It is frequently also necessary to monitor for threshold-exceeding values of explosive and/or toxic mixtures, e.g. sulphur compounds. These measures are not only costly but are subject to a risk of unsatisfactory operation. Air scavenging also does not free the user from having to use explosionproof analyzer systems, in order to protect the same with respect to external expolosion risks and protect the environment against explosions, which could result from the ignitable materials in the analyzer system.

Even in the case of external ventilation of an analyzer shelter, particulary if there are several analyzer system possible exit quantities of flammable materials will lead to the lower explosion limit of the air/gas mixture being exceeded. The disconnection of the remaining analyzer systems and all electrical equipment in the shelter necessary for safety reasons is in most cases not acceptable for practical uses.

It is therefore unavoidable that the individual analyzers must be of an explosionproof construction. Possible explosion protection types are oil encapsulation, overpressure encapsulation, sand encapsulation and pressure-resistant encapsulation for increased security and intrinsic safety.

It is disadvantageous that, as a result of the mechanical construction of the explosion protection means, particulary in the case of pressure-resistant encapsulation, the accessibility to the internal components of the analyzer is impeded. This leads to long repair times and to low apparatus availability. In addition, fault detection is very complicated, because after opening the explosion protection means the analyzers must either be put out of operation or, because instead of this, it is constantly necessary to check the environment to ensure that it is free from explosion risks. A third complicated possibility is to ensure accident-free repairs or fault detection by special work protection, e.g. by a "hot work approval". A further disadvantage is that signal line passages through a casing with pressure-resistant encapsulation are subject to limitations in their numbers and all the signalling means for the remaining units of the analyzer system must have explosion protection. If an evaluation computer is provided, the latter must also be explosionproof, which once again leads to considerable technical and costly precautions.

Another disadvantage of an analyzer system with an analyzer shelter is that the point of installation cannot be freely selected as a result of the size of the system. As it is possible to enter an analzyer shelter, escape routes must also be kept free for staff. For safety reasons, access by a member of staff can only take place if somebody else is available for supervision and providing assistance in the case of an emergency. Thus, the analyzer system cannot be located in the vicinity of the process to be analyzed and therefore long supply lines and pumping equipment must be provided. As a result of the necessarily occurring clearance volumes and idle times, this is disadvantageous for measuring reasons.

Thus, the known analyzer systems have not been used to the extent and at the locations within a process, such as would be desirable for economic and measuring reasons.

BRIEF SUMMARY OF THE INVENTION

It is accordingly an object of the present invention to provide a novel and improved analyzer system which can be economically manufactured and operated and whose availability is improved.

According to the present invention there is provided in a self-supporting and sealed housing at least one extractable support member largely taking up the interior of the housing, the support member is connected at its front side with a first door member closing the extraction opening, and carries at least one process analyzer, at least one sample preparation means, at least one auxiliary material system and an unidirectional or bidirectional communications means for electrical signals, the support member being connected via flexible supply and disposal lines with the stationary housing part, access to the housing is provided with a door closing means coupled via monitoring means to an explosion and/or environment protection means in such a way that opening is only possible in a safe state and, on the outside of the housing, there is provided at least one keyboard and observation station for locally checking the complete system.

The invention is very economical, particularly as a result of the small housing. The analyzer system can be completely assembled and tested in the factory, so that only minimum inspection and assembly expenditure is necessary at the point of installation. The dimensions also make it possible, in most cases, to find an installation point close to the process, so that no long and therefore costly supply and discharge lines, or process return and pressure raising means are required. The invention provides the advantage that explosion and weather protection can be achieved with a single housing, so that an explosionproof zone is formed within the housing. Thus, an explosion protection is provided by the housing, this need not be achieved through the construction of the analyzers, so that the latter can have standard designs. As a result the operating staff require no special training and no special spares or tools are required for maintenance purposes.

In addition, an optimum protection against hazardous materials is achieved. As the housing can be tightly closed and as only, a relatively small scavenging quantity is necessary, it is possible to provide washing and scavenging cycles through using a self-sufficient circulation. Therefore highly effective inert gases can be used and also a largely self-sufficient auxiliary material supply can be achieved. It is also possible to minimize the manufacturing and operating costs for air conditioning of the housing interior.

Another important advantage of the invention is the compact construction of the analyzer system when the housing is closed. However, optimum accessibility is ensured for replacement, repairing and maintaining units if the support member is extended from the housing.

Another important advantage of the invention is the high availability of the analyzer system. Practical tests have revealed that a 90% availability can be achieved. This is brought about in that the "explosion-free" atmosphere in which all the units are housed permits the use of standard sensors in a virtually random number. It is also possible to arrange even extensive electronic evaluation units within the housing, without any restriction being required with respect to explosion protection. With the aid of an electronic fault diagnosis system, function monitoring and fault detection can take place with the housing closed. There can also be a data teletransmission of the diagnosis data to a central station and a continuous monitoring of the test signals for plausibility and error limits. A fault diagnosis system reduces the repair times, in which is normally included error detection and location. In addition, minimum demands are made on the diagnosis staff.

Tried and tested measuring methods and equipment can be used in the design of the fault diagnosis system. There is no restriction to equipment which just happens to be available in an explosionproof version. There are no technical and commercial restrictions regarding the arrangement and routing of lines, because inexpensive standard constructions can be used.

Availability is also increased in that a rapid replacement of complete analyzer systems is possible, e.g. for carrying out a major overhaul in a workshop. To this end, it is merely necessary to remove the door member and the support member connected thereto and replace same by another. Systematic errors and faults in the units are reduced by inner area air conditioning. Any chance faults which occur are immediately detected and indicated by the fault diagnosis system.

The explosion-protected inner area offers the possibility of providing freely selectable analyzer combinations. This has the advantage that improved combinatory measuring methods can be performed and that correlative and redundant measurements can be carried out. The invention also offers many advantages regarding the protection of operating personnel and the environment. Through the locking of the door member combined with the monitoring means access to the interior of the housing is controlled in such a way that opening is prevented in a dangerous state. Thus, maintenance can also be carried out by untrained staff and the explosion protection is independent of the care exercised by servicing staff. As a result of the very tight, insulating housing the requirements for a circulation of the internal gas volume are satisfied. It is possible without difficulty to use the protection types "external ventilation" and "overpressure encapsulation" for the entire housing. In the case of economic use, these protection types offer the minimum use restrictions. Through the use of inert gases for scavenging purposes and as an ignition protection, there is no risk of saturation with flammable gases. The pressure-tight housing requires minimum ignition protection gas quantities. There is also no need for permanent scavenging and compensation of leakage losses. As a result of a slight overpressure in the inner area, it is possible to prevent any penetration of the external atmosphere.

When using an ignition protection gas, it is also possible to construct cooling or heating means with non-explosionproof designs. If a self-sufficient water circulation is provided for analyzer cooling purposes, there is no need for water treatment means of the type required when cooling water has to be taken from external sources.

The circulation of the inert protective gas for avoiding dead corners necessary for explosion protection reasons can be linked in simple manner with air conditioning, so that independently of the particular analyzer system installed, largely in the form of small, complex process systems, as well as environmental conditions, it is possible to ensure a regulated inner area temperature.

The housing also makes it possible to install all auxiliary systems necessary for the operation of an analyzer under the same explosion-protected conditions and independent of environmental conditions, such as cold, heat, corrosion, etc.

With regards to the housing, it is pointed out that protection against explosions, weather and contact with health-prejudicial materials is ensured. As a result of the automatic door, automatic energizing takes place of a testing, switching on and switching off system. The interior of the housing can only be entered by the operator when the programmed safety procedure releases the automatic door system. The analyzer system only starts operating when an adequate explosion protection is ensured in the interior of the housing, i.e. when the units of the entire system are no longer accessible to the operator.

Apart from the economic advantages and the high availability, a further advantage of the invention is the minimizing of accident risks. As the diagnosis system covers all units of the entire analyzer system and as a result of a corresponding redundancy operates clearly and free from inherent errors, it is possible to clearly locate errors within individual units. This prevents opening and closing of the house and putting into operation only being possible when the analyzer system is in a safe state. This includes checking hot surface and electrical equipment for the capacity to ignite a flammable mixture and that inert gas is mixed with oxygen prior to opening the protective housing in order to exclude health hazards. However, prior to putting into operation no atmospheric oxygen must be in the protective housing. As there is no need to separately provide the units with explosion protection means, there is no need to handle such means. Thus, there is no risk that e.g. on closing the pressure-tight encapsulation or overpressure encapsulations for individual units of operating errors being made which could lead to accidents. There is obviously also no need to take account of assembly-relating regulations when fitting equipment, which would otherwise have to be taken into account, e.g. in the case of the protection type intrinsic safety.

BRIEF DESCRIPTION OF THE DRAWINGS

Further aspects, features and advantages of the present invention are described in greater detail hereinafter with reference to a preferred embodiment thereof and the drawings, wherein:

FIG. 5 shows diagrammatically a perspective view of several analyzer systems according to the previous drawings.

DESCRIPTION OF THE PREFERRED EMBODIMENTS

Figure 1:
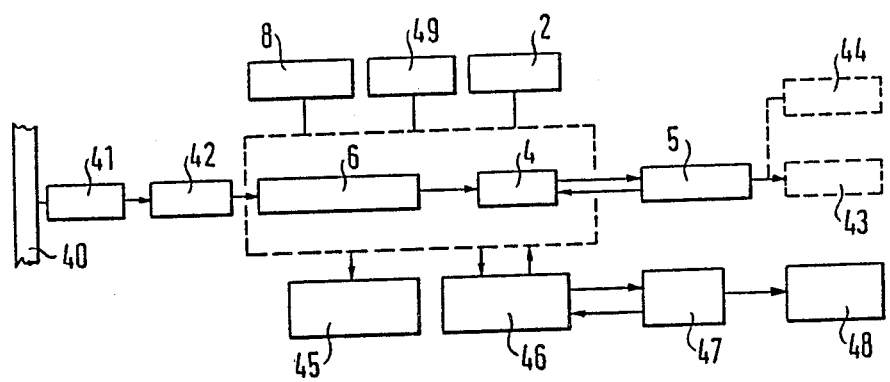
FIG. 1 shows a block diagram of an analyzer system.

FIG. 1 diagrammatically illustrates the individual components and subsystems of a process analysis system, as well as the interaction of the individual components. Thus, a process 40 leads to material sample taking 41 and sample supply 42 to a sample preparation 6. The prepared samples are then supplied to one or more analyzers 4 linked by a bidirectional line to an electronic control and signal converter unit 5. Between analyzer 4 and control 5 instructions are exchanged in one direction and test signals in the other. The control 5 can be connected to a control room 43 and a laboratory 44. For the operation of the analyzer system, it is necessary to have at least one calibrating medium from a calibrating system 8, auxiliary materials or adjuvants 49 and a disposal means 45. The analyzer system also includes a gas-tight housing 2, as well as a fault diagnosis arrangement 46, which can be connected via a control and signal processing unit 47 e.g. to a test workshop 48. The fault diagnosis arrangement 46 receives instructions from the control and signal processing unit 47 and returns diagnosis signals in the opposite direction.

Figure 2:
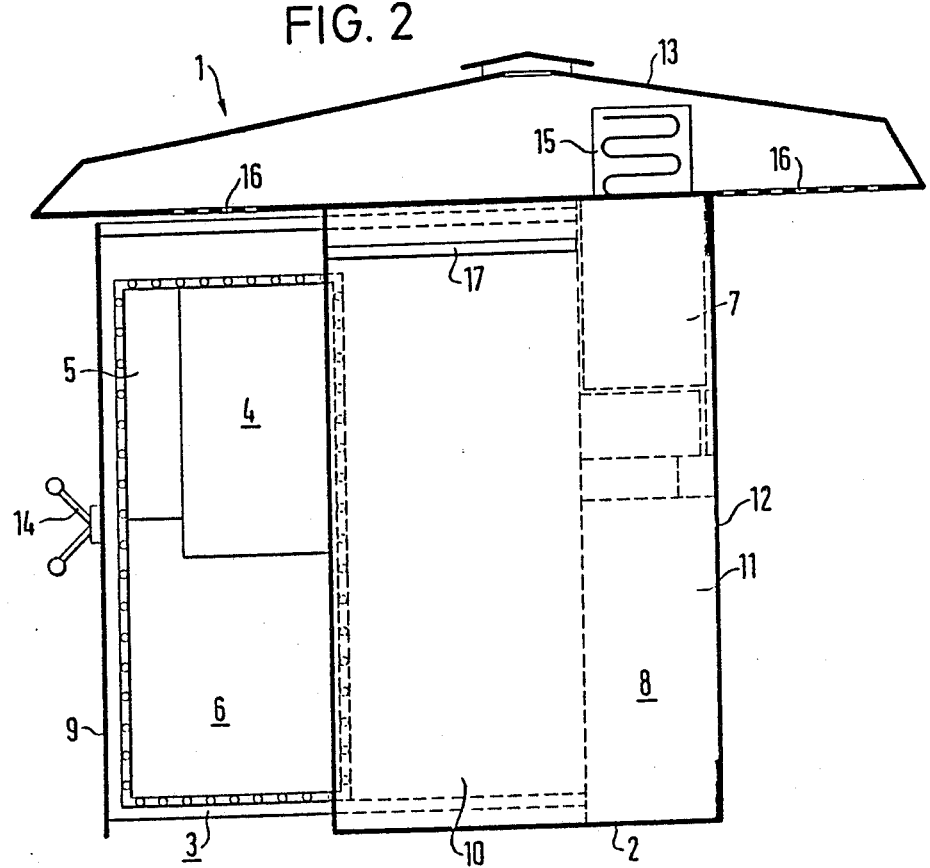
FIG. 2 shows diagrammatically a longitudinal section through an analyzer system.

According to FIG. 2 analyzer system 1 comprises the self-supporting housing 2, a support member 3 which is extendible from the housing 2, a plurality of analyzers 4, electronic control means 5, sample preparation means 6, a cooling system 7 and a calibration system 8. FIG. 2 illustrates the state in which the support member 3 has been extended from the housing 2, so that it is freely accessible from two sides, whilst its front side is taken up by a first door 9. For ease of illustration, it is not shown in FIG. 2 that the support member 3 is mounted on telescopic rails. The support member 3 serves as an assembly frame for the analyzers 4, the electronic control 5 and the sample preparation means 6. These are technically top quality components and equipment. The other auxiliary equipment necessary for operating the analyzer system, such as e.g. the cooling system, or storage tanks and auxiliary material lines, such as the calibration system, are housed in a stationary manner in the housing 2. Although these items of equipment could fundamentally be installed on support member 3, in the case of more comprehensive analyzer systems, like that e.g. shown in FIG. 2, it can be advantageous to provide a first housing area 10 for receiving the support member 3 and a second area 11 in a stationary portion of the housing 2 for receiving the stationary equipment. Access to the second area 11 is provided by a second door 12 fitted to the front. As it can be assumed that access is seldom desired or required to the area 11, the second door 12 is preferably detachably bolted to the housing 2. This makes it possible, by taking relatively simple sealing measures, to achieve an adequately tight sealing of the door opening. For closing the first door 9, a plurality of pneumatically operatable cylinders or equivalent devices are provided, which are uniformly distributed along the circumference of the door opening (not shown). By operating a control member 14, a uniform operation of these devices is effected, so that the first door 9 is uniformly and firmly pressed against the corresponding sealing surfaces on the housing 2. These measures make it possible to tightly close to a very high degree the two openings of housing 2 by means of the first and second doors 9, 12, so that the housing 2 has an overall very good gas-tight sealing.

A projecting gable roof 13 is arranged on the housing 2. Roof 13 projects so far over the narrow sides of the housing 2 that is completely covers the extraction area of the support member 3 and also protects the access to area 11. Below the roof 13 or in the outer wall of the second door 12, there is provided a condenser which can have a large-area construction and is connected to the cooling system 7. Below the projecting roof surfaces are provided air intakes 16 protected with filters. The entering air can escape under the coping from the otherwise closed roof area. Within the sealed housing 2, below the container top an air duct 17 extends from the cooling system 7 into the first area 10, so that a circuit is obtained, which is clockwise in the presently represented embodiment.

Figure 3:
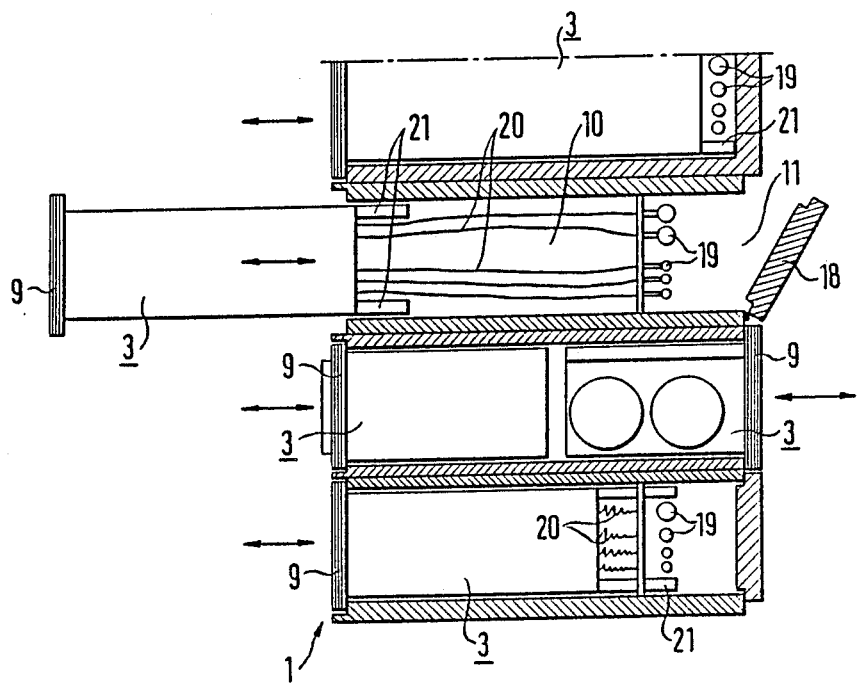
FIG. 3 shows diagrammatically a cross-section through several juxtaposed analyzer systems according to FIG. 2.

FIG. 3 illustrates how an analyzer system described in FIG. 2 with several similar systems can be arranged in a juxtaposed row in a space-saving manner. The examples of analyzer system shown in FIG. 3 have different designs. The upper system is only provided with a single outlet extending over the entire length of housing 2, whilst the back surface is closed by a wall. As the access to all the components can take place via support members 3, it is possible to set up the rear of housing 2, e.g. on a wall.

Furthermore, in this embodiment another support member 3 which is again in the first area 10 and in this case, the second area 11 is closable by a hinged door 18 and again serves for the arrangement of stationary components.

The third analyzer system comprises two support members 3, which are in each case movable in the directions of their respective lowermost arrows from respective ones of the narrow sides of housing 2. The analyzer system, as viewed in FIG. 3, essentially corresponds to that of the previous paragraph. It is merely shown in the closed state of the housing. In place of the hinged door, a boltable door is diagrammatically shown.

At the opposite end of the support member 3 to the first door 9 are provided connections 19 for all the auxiliary material lines and for those lines supplying or removing the substances to be analyzed. The auxiliary materials include cooling agents and heating steam, apart from the materials directly required for analysis purposes. These connections are connected by flexible lines 20 to the respective support member 3. Flexible lines 20 also comprise connections for carrying electrical control and test signals and for supplying electric power.

In FIG. 3 it is also possible to see the telescopic rails 21, on which the support members 3 are guided. It is also possible to see the cross-section of the first door 9, for which a multilayer construction is adopted, an inner layer being constituted by a thermally insulating material and the outer layers by a material resistant the atmosphere. This multilayer construction corresponds to that of the housing walls.

Figure 4:
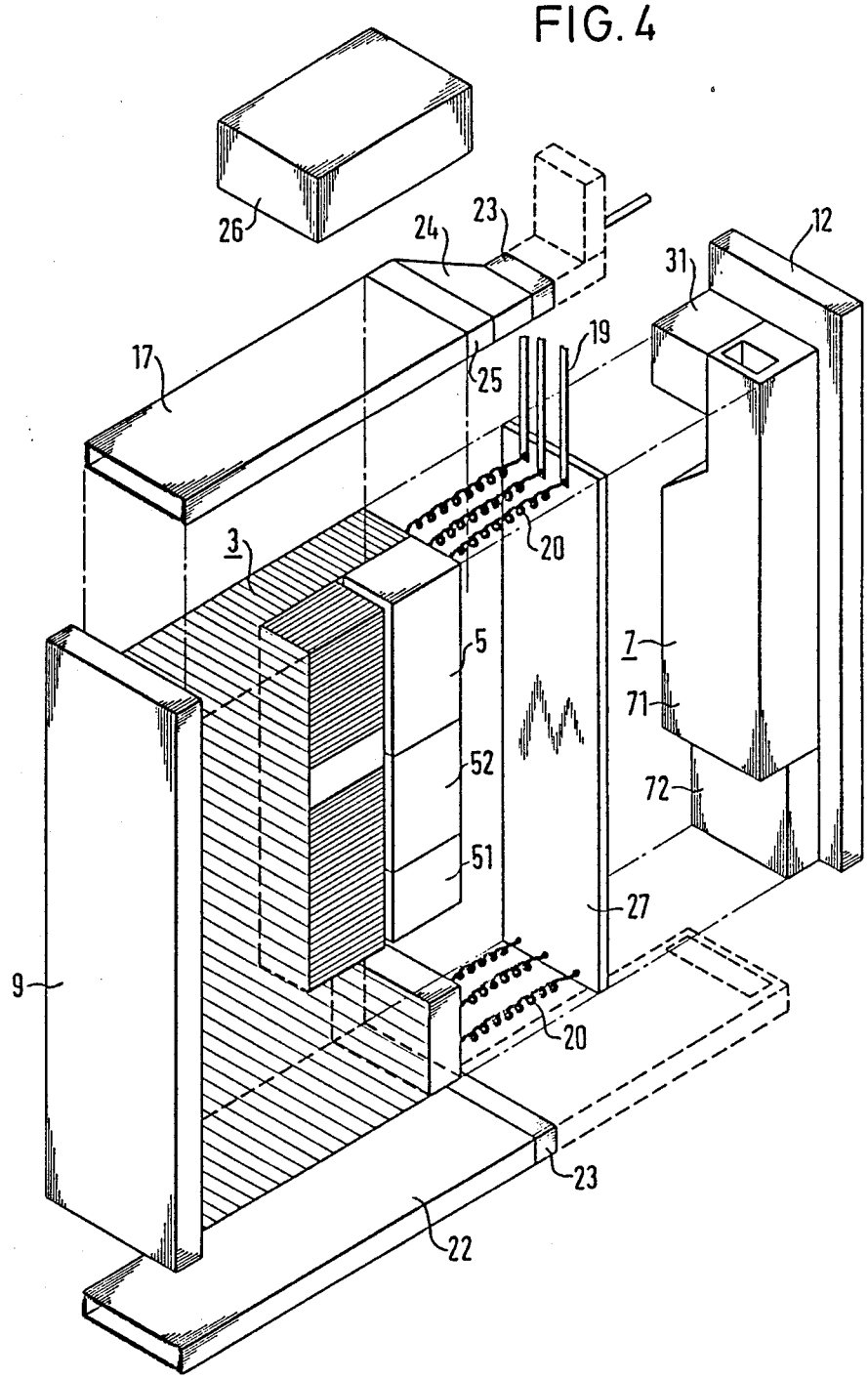
FIG. 4 shows diagrammatically an exploded view of the analyzer system according to FIG. 2.

FIG. 4 further illustrates the individual components of the analyzer system, an exploded view being chosen to make viewing easier. The following components are provided on support member 3: the sample preparation means (not shown), whose point of installation is indicated by oblique lines, one or more analyzers (not shown), whose point of installation is indicated by cross lines, in conjunction with the sample preparation and analyzer units a measuring means (not shown), a connection unit 51 for electrical lines, a unit 52 for distributing and securing the electric power supply and electric signal and measuring lines and electronic control 5, which comprises a fault diagnosis system. Fault diagnosis systems comprise an electronic computer, which is connected via sensors to the components to be monitored.

The electronic control 5 also comprises an opening and closing monitoring system for the first door 9. This system is also connected to sensors, by means of which critical limit values can be monitored. If these values were exceeded, opening of the first door 9 would lead to an explosion risk state or would endanger the operator in some other way, e.g. by the escape of toxic gases. The opening and closing monitoring means therefore ensures that the closure of the first door 9 is only permitted when hot surfaces have cooled to below the ignition temperature, possibly scavenging and spraying equipment have been operated, carcinogenic or toxic gases have possibly been washed out and possibly an overpressure or underpressure have been restored to normal pressure. This automatically prevents critical situations. It is also ensured that, when the analyzer system is put into operation, the atmospheric oxygen which has entered is blown out and equipment is only put into operation after checking all the safety equipment.

The essential sensors for the opening and closing monitoring system are so-called monitoring sensors, which are arranged at all critical points within the housing 2. If a danger is detected, this is of course also indicated by indicating or display units outside the housing and an acoustic or optical alarm is given. Simultaneously, the measures described in connection with door opening are performed, in order to remove the critical situation.

Such monitoring sensors 23 can be located in the upper air duct 17 and in the lower air duct 22 at points of connection to the first area 10 or at the inlet/outlet with respect to cooling system 7. In addition, all the line passages and outlets from the housing are constructed in explosionproof manner. Following the monitoring sensor 23 located at the inlet of air ducts 17 or 22 are provided a fan 24 and then a heater 25. Air duct 22 can be simultaneously constructed as a floor trough or can directly pass into the latter for collecting drips, which may pass from within the system. In addition, the lower air duct 22 can be used for stabilizing housing 2.

Above the upper air duct 17 in the present embodiment there is provided a spraying means 26, which can function according to the dish washer principle, by which the support member 3 and all components on it are sprayed with a liquid.

In the right-hand area of the housing the cooling system 7 is fitted to the back of the second door 12 and comprises an air cooler 71 and a water heat exchanger 72. In the present embodiment the second door 12 simultaneously serves as a condenser for removing cooling heat. It can be clearly seen that the cooling system 7 provides a connection for the cooling medium between the lower and upper air duct 22, 17. In the present embodiment, an electrical main connection 31 is fitted to the second door 12 and is connected to an external master switch (not shown). Between the right and left inner areas there is installed a partition 27.

FIG. 5 shows how several analyzer systems according to FIG. 3 are arranged in line and connected to form a compact unit, without restricting access to the analyzers 4. The manner in which the connecting lines 19 can be led from the process to be analyzed to the analyzer systems can be seen. If, as shown here, a plurality of the support members 3 are juxtaposed, it is advantageous to provide on the outside of the first door 9 operating, indicating and monitoring elements 28, 29, 30. Operating elements 28 more particularly serve to control the supply and removal of auxiliary materials.

Typical dimensions for housing 2 are e.g. 0.7×1.2 m for the base surface and 2.2 m for the height.

I claim:

1. A process analyzer system comprising:
   at least one means for preparing samples;
   at least one process analyzer;
   at least one auxiliary material system;
   unidirectional or bidirectional communications means for transmitting electrical signals;
   self-supporting and sealed housing means for enclosing a housing interior in an explosion-proof manner;
   said housing means comprising a stationary housing part, a door member and an opening in said stationary housing part and said door member serving to close said opening;
   movable support means for carrying said process analyzer, said means for preparing samples, said auxiliary material system and said unidirectional or bidirectional communications means;
   means for mounting said support means for displacement to and from the housing interior of said housing means through said opening;
   said support means being connected at a front side thereof with said door member;
   flexible supply and disposal lines connecting said support means to said stationary housing part;
   means for closing said door;
   means for protecting said system against an explosion and/or against the environment;
   monitoring means for coupling said door closing means to said explosion and/or environment protection means so that opening of said door member is only possible in a safe state; and
   at least one keyboard and observation station provided on the outside of said housing means for locally checking said system.

2. A process analyzer system according to claim 1, wherein said support member is fully extendible from said stationary housing part through said opening.

3. A process analyzer system according to claim 1, wherein said housing means has walls of a multilayer construction with at least one central insulating material layer.

4. A process analyzer system according to claim 1, including means for closing said door member.

5. A process analyzer system according to claim 1, including means for effecting spraying or washing within said housing.

6. A process analyzer system according to claim 1, wherein said housing means is provided with a tight floor trough or a collecting container.

7. A process analyzer system according to claim 1, wherein said support means are extended from a narrow side of said housing means.

8. A process analyzer system according to claim 1, including a fault diagnosis system carried by said support means.

9. A process analyzer system according to claim 1, further comprising a calibrating material container in said housing means.

10. A process analyzer system according to claim 1, further comprising a self-sufficient cooling water system.

11. A process analyzer system according to claim 1, further comprising means for subdividing said housing means into a first area for receiving said support means and into a second area for receiving stationary equipment.

12. A process analyzer system according to claim 11, further comprising an additional door member provided on said housing means to give access to said second area.

13. A process analyzer system according to claim 1, wherein said housing means is provided with a projecting roof.

14. A process analyzer system according to claim 13, wherein said roof projects completely over said support means when said support means is in fully extended position.

15. A process analyzer system according to claim 13, wherein means for suspending a protective curtain are provided along said roof and projecting over said fully extended position of said support means.

16. A process analyzer system according to claim 1, further comprising means for air conditioning said housing means.

17. A process analyzer system according to claim 1, wherein said housing means comprise means for enclosing the housing interior in a gas-tight manner and a fire-extinguishing gas fills the housing interior.

* * * * *